US006849725B2

(12) United States Patent
Junghans et al.

(10) Patent No.: US 6,849,725 B2
(45) Date of Patent: Feb. 1, 2005

(54) COVALENTLY CLOSED NUCLEIC ACID MOLECULES FOR IMMUNOSTIMULATION

(75) Inventors: Claas Junghans, Berlin (DE); Burghardt Wittig, Berlin (DE); Sven König Merediz, Berlin (DE); Matthias Schroff, Berlin (DE)

(73) Assignee: Mologen Forschungs Entwicklungs und Vertriebs GmbH, Berlin (DE)

( * ) Notice: Subject to any disclaimer, the term of this patent is extended or adjusted under 35 U.S.C. 154(b) by 197 days.

(21) Appl. No.: 10/057,311

(22) Filed: Jan. 24, 2002

(65) Prior Publication Data

US 2003/0125279 A1 Jul. 3, 2003

Related U.S. Application Data

(63) Continuation-in-part of application No. PCT/DE00/00565, filed on Feb. 24, 2000.

(30) Foreign Application Priority Data

Jul. 27, 1999 (DE) ......................................... 199 35 756

(51) Int. Cl.[7] .......................... C07H 21/02; C07H 21/04
(52) U.S. Cl. .................................................... 536/23.1
(58) Field of Search ...................... 435/6, 91.1, 91.31, 435/455; 514/44; 536/23.1, 24.5

(56) References Cited

U.S. PATENT DOCUMENTS

| 5,663,153 A | 9/1997 | Hutcherson et al. |
| 5,723,335 A | 3/1998 | Hutcherson et al. |
| 5,750,669 A | 5/1998 | Rösch et al. |
| 5,856,462 A | 1/1999 | Agrawal |

FOREIGN PATENT DOCUMENTS

| EP | 0855184 | 7/1998 |
| FR | 2732971 | 10/1996 |
| WO | 9818810 | 5/1998 |
| WO | 9821322 | 5/1998 |

OTHER PUBLICATIONS

Krieg et al. Immunology Today, vol. 21, No. 10, pp. 521–526 (2000).*
Weiner, G. J. Leukocyte Biol. vol. 68, pp. 455–463 (2000).*
Agrawal et al. Molecular Med. Today, vol. 6, pp. 72–81 (2000).*
McCluskie et al. Molecular Med. vol. 5, No. 5, pp. 287–300 (1999).*
Erie, D. et al. Biochemistry, vol. 26, No. 22, pp. 7150–7159 (1987).*
Wolters, M. et al. Nucleic Acids Res., vol. 17, No. 13, pp. 5163–5172 (1989).*
Kreig AM, Yi AK, Matson S. Waldschmidt TJ, Bishop GA, Teasdale R, Koretzky GA, Klinmän DM;(CpG motifs in bacterial DNA trigger direct B–cell activation; Nature Apr. 6, 1995 374;6522 546–9.

Seder RA and Paul WE, Acquisition of lymphokine–producing phenotype by CD4+ T cells; Annu Rev Immunol. 1994;12:635–73.

Melief CJ, Kast WM; T cell immunotherapy of cancer; Res Immunol Jun. Aug. 1991;142(5–6);425–9.

Pasternak G, Hochhaus A, Schultheis B, Hehlmann R; Chronic myelogeneous leukemia: molecular and cellular aspects: J Cancer Res Clin Oncol 1998;124(12):643–60.

Weber LW, Bowne WB, Wolchok JD, Srinivasan R, Qin J, Moroi Y, Clynes R, Song P, Lewis JJ, Houghton AN; Tumor immunity and autoimmunity induced by immunization with homologous DNA; J Clin Invest Sep. 15, 1998;102(6):1258–64.

Surman DR, Irvine KR, Shulman EP, Allweis TM, Rosenberg SA, Restifo NJ; Generation of polyclonal rabbit antisera to mouse melanoma associated antigens using gene gun immunization; Immunal Methods; May 1, 1998;214(1–2):51–62.

Kovarik J, et al. CpG oligodeoxynucleotides can circumvent the Th2 polarization of neonatal responses to vaccines but may fail to fully redirect Th2 responses established by neonatal priming; J Immunol. Feb. 1, 1999;162(3):1611–7.

Krieg AM, Wu T, Weeratna R, Efler SM, Love–Homan L, Yang L, Yi Ak, Short D, Davis HL; Sequence motifs in adenoviral DNA block immune activation by stimulatory CpG motifs; Proc Natl Acad Sci U S A Oct. 13, 1998;95(21):12631–6.

Kreig AM, CpG DNA: a pathogenic factor in systemic lupus erythematosus?, J Clin Immunol Nov. 1995;15(6) :204–92.

Sheehan and Lan, Phosphorothioate Oligonucleotides Inhibit the Intrinsic Tanase Complex, Blood 92, 1617–1625(1998).

Lim et al., Sequence–independent inhibiton of RNA transcription by DNA dumbbells and other decoys, 1997, Nuc. Acids Res. 25, 575–581; Blumenfeld et al., Nuc. Acids Res. 1993, 21, 3405–3411.

Weeratna R, Brazolot Millan CL, Krieg AM, Davis HL; Reduction of antigen expression from DNA vaccines by coadministered oligodeoxynucleotides. Antisense Nucleic Acid Drug Dev Aug. 1998;8(4):351–6.

(List continued on next page.)

Primary Examiner—John L. LeGuyader
Assistant Examiner—Jane Zara
(74) Attorney, Agent, or Firm—Nils H. Ljungman & Associates

(57) ABSTRACT

Short deoxyribonucleic acid molecules that are partially single-stranded, dumbbell-shaped, and covalently closed, which contain one or more unmethylated cytosine guanosine motif (CpG motif) and exhibit immunomodifying effects. Such molecules can be used for immunostimulation applications in humans or vertebrates.

8 Claims, 4 Drawing Sheets

OTHER PUBLICATIONS

Immunostimulatory oligodeoxynucleotides promote protective immunity and provide systemic therapy for leishmaniasis via IL–12– and IFN–gamma–dependent mechanisms, Walker et al., Proc Natl Acad Sci USA Jun. 8, 1999 96:12 6970–5.

Clusel C et al: "Ex Vivo Regulation of Specific Gene Expression by Hanomolar Concentration of Double–Stranded Dumbell Oligonucleotides" Nucleic Acids Research,GB,Oxford University Press, Surrey, vol. 21, No. 15, Jul. 25, 1993, pp. 3405–3411, XP000572382 ISSN: 0305–1048 the whole document.

Krieg A M et al: "Oligodeoxyncleotide Modifications Determine the Magnitude of B Cell Stimulation by CPG Motifs" Antisense & Nucleic Acid Drug Development, US,Mary Ann Liebert, Inc., New York, vol. 6, No. 2, 1996, pp:133–139, XP000610233 ISSN: 1087–2906 the whole document.

Erie D et al: "A Dumbell–Shaped Double–Hairpin Structure of DNA: A Thermodynamicinvestigation" Biochemistry 1987, XP002027687 the whole document.

Hosona et al, Properties of Base–Pairing in the Stem Region of Hairpin Antisense Oligonucleotides Containing 2'–Methcxynucleosides, Biochim Biophys, Acta 244, 339–344 (1995).

* cited by examiner

COVALENTLY CLOSED NUCLEIC ACID MOLECULES FOR IMMUNOSTIMULATION

CONTINUING APPLICATION DATA

This application is a continuation-in-part of International Patent Application No. PCT/DE00/00565 filed Feb. 24, 2000, which claims priority to Federal Republic of Germany Patent Application No. 199 35 756 filed Jul. 27, 1999. International Patent Application No. PCT/DE00/00565 was pending as of the filing date of this application. The United States was an elected state in International Patent Application No. PCT/DE00/00565. The priority of International Patent Application PCT/DE00/00565 and Federal Republic of Germany Patent Application No. 199 35 756 are each hereby expressly claimed.

FIELD OF THE INVENTION

The present invention relates to short deoxyribonucleic acid molecules that are partially single-stranded, dumbbell-shaped, and covalently closed, which contain one or more unmethylated cytosine guanosine motif (CpG motif) and exhibit immunomodifying effects. The present invention also relates to uses of such deoxyribonucleic acid molecules for modulating the activities of human or animal immune systems.

BACKGROUND OF THE INVENTION

It has been known for several years that certain short nucleic acid sequences are able to demonstrate a significant physiological effect, by stimulating effector cells in the immune system via unknown mechanisms. These short nucleic acid sequences, which are generally referred to as immunostimulatory nucleic acid sequences (ISSs), are only a few bases in length, and their functions are usually not dependent upon expression of proteins encoded by them.

Most known immunomodifying cytosine oligodeoxyribonucleotide sequences (ODNs) contain at least one CpG motif. Krieg et al., *CpG Motifs in Bacterial DNA Trigger Direct B-Cell Activation,* Nature 374:6522 546–9 (Apr. 6, 1995). The occurrence of CpG motifs in the genome of eukaryotes is substantially less than that in the genome of prokaryotes. It is therefore suggested that recognition of CpG motifs by eukaryotic cells may be used as a warning signal to indicate infection by prokaryotic pathogens. For instance, recognition of the CpG motifs by the eukaryotic cells may lead to certain emergency responses in the cells, which then trigger a reaction directed against the viral or bacterial pathogens, independently of or prior to the production of a T-helper cell immmunoresponse. In fact, CpG motifs trigger certain CpG-dependent signal paths, which generates costimulatory signals that are required for activating T-cells and B-cells, in particular for the secretion of cytokines by a cellular Type-1 response (Th1-specific cytokines such as interferon gamma, IL-7, IL-12), thus enabling stimulation and proliferation of B-cells independent of T-helper cells. Moreover, the activities of the Type-2 cytokines (such as IL-4 and IL-10) are suppressed by such CpG-dependent signal paths, probably because of the antagonism effect between Type-1 and Type-2 responses. Sedar & Paul, *Acquisition of Lumphokine-Producing Phenotype by CD4+ T Cells,* Annual Rev. Immunol., 12:635–73 (1994).

The potential of using nucleic acid molecules containing CpG motifs to modulate the immunoresponse is considerable, which has generated sudden and widespread scientific interest in exploiting the therapeutic and prophylactic applications of such molecules.

It has been discovered that CpG motifs are more effective as immunostimulators when they exist as single-stranded molecules. See WO98/18810 A1, S. 17, II 29–30. Therefore, numerous experimental approaches aiming to treat infectious illnesses, tumors, and/or autoimmune diseases use short, open-chain, single-stranded ISS oligodeoxynucleotides that contain CpG motifs.

However, the open-chain, single-stranded ISS oligodeoxynucleotides degrade very quickly in vivo, due to impacts by extracellular and intracellular exonucleases. Moreover, the active single-stranded ISS molecules, due to their instability, are too toxic for direct use in human medical applications. Therefore, the use of isolated ISS oligodeoxynucleotides in in vivo applications is not practicable. They have to be either modified before in vivo administration or introduced into vector sequences. WO98/18810 A1; Weeratna et al., *Reduction of Antigen Expression from DNA Vaccines by Coadministered Oligodeoxynucleotides,* Antisense Nucleic Acid Drug Dev., 8(4):351–6 (August 1998).

Extracellular and intracellular exonucleases have been found to display significantly reduced enzymatic activity when modified phosphor-ester bonds are formed in the backbone of the open-chain, single-stranded ISS oligodeoxynucleotides. This discovery has led to use of phosphor thioesters ("thioates") or reduced phosphor bonds (phosphonates) in chiral or achiral form to stablize the open-chain, single-stranded nucleic acid molecules that are to be administered to patients.

These modified bonds can be produced by the solid phase synthesis method. However, such method is much more complicated than the classic DNA amidites synthesis method. Moreover, during clinical studies of antisense strategies, where these modified bonds are frequently used, it was discovered, that these modified bonds cause considerable amount of side effects, particularly on the blood coagulation system and the complementary system. Sheehan & Lan, Blood 92, 1617–25 (1998). Furthermore, when these modified bonds are introduced into the ISS molecules to form thiophosphoric acid derivatives for the purpose of stabilizing the ISS molecules, the resulted ISS molecules display less stimulatory activities, due to the fact that the CpG motifs, which are required for the stimulatory activities to be effectuated, are themselves protected by the flanking sequences. WO98/18810 A1.

WO98/18810 A1 comprehensively describes the theories concerning use and production of immunostimulatory ISS molecules containing CpG motifs. It also presents several solutions to the problem of in vivo instability of such molecules, including formation of thiophosphate esters, dithiophosphate esters or phosphonates and creation of secondary structures (such as a stem-loop). However, these solutions presented and suggested by WO98/18810 are expressly limited to single-stranded linear ODNs.

U.S. Pat. Nos. 5,663,153, 5,723,335, and 5,856,462 disclose production and use of phosphorothioate oligomers in connection with ISS molecules.

U.S. Pat. No. 5,750,669 suggests a different approach for protecting open-chain, single-stranded ISS molecules, which relates to linking the ends of the oligomers with nucleoside residues via 5'-5' and 3'-3' bonds, which functions to block exonucleolytic degradation of the ISS molecules.

Hoson et al., Biochim. Biophys. Acta. 244, 339–344 (1995), disclose formation of linear oligodeoxynucleotides with a stem-loop structure at the 3' end, which can be used for antisense research.

Double stem-loop or covalently closed, dumbbell-shaped ODNs are known from experimental approaches that focus on competition in bonding sites for DNA-binding proteins and transcription factors. Lim et al., Nuc. Acids Res. 25, 575–581 (1997); Blumenfeld et al., Nuc. Acids. Res. 21, 3405–3411 (1993).

OBJECT OF THE INVENTION

Based on this state of the art, the present invention sets out to provide suitable molecular structures containing immunostimulatory and/or immunomodifying deoxyribonucleotide sequences, which are sufficiently stable to tolerate the degradative effects of exonucleases, while still exhibiting significant immunostimulatory and/or immunomodifying effects.

SUMMARY OF THE INVENTION

The present invention in one aspect relates to short deoxyribonucleic acid molecules, comprising a partially single-stranded, dumbbell-shaped, covalently closed sequence of nucleoside residues, and containing one or more sequences of the formula:

$N^1N^2CGN^3N^4$ wherein:
$N^1N^2$ is selected from the group consisting of GT, GG, GA, AT, and AA;
$N^3N^4$ is selected from the group consisting of CT, TT, C deoxycytosine, G deoxyguanosine, A deoxyadenosine, and T deoxythymidine.

Such dumbbell-shaped, covalently closed deoxyribonucleic acid molecules have no free 5' or 3' ends, and they are therefore undegradable by exonucleases.

Such covalently closed deoxyribonucleic acid molecules can be obtained from open-chain deoxyribonucleic acid molecules that have a partially self-complementary sequence, which, either together with each other or with a second molecule, are able to create an intermediary stable hybrid having a closed double-stranded area with a gap in the sugar phosphate backbone, by ligation of the gap in the backbone using a suitable enzyme (such as a DNA ligase derived from a T4 bacteriophage).

Alternatively, such covalently closed molecule can be obtained by intramolecular ligation of a molecule which has at least two self-complementary areas, separated only by a gap in the phosphate backbone.

It is preferred that the short deoxyribonucleic acid molecules of the present invention have a chain length within the range of from about 40 to about 200 nucleotides, and more preferably within the range of from about 48 to about 116 nucleotides.

It is also preferred that the base sequence $N^1N^2CGN^3N^4$ is in the single-stranded portion of such partially single-stranded, dumbbell-shaped, covalently closed deoxyribonucleic acid molecule of the present invention.

One aspect of the present invention relates to a partially single-stranded, dumbbell-shaped, covalently closed deoxyribonucleic acid molecule comprising at least one of the following base sequence:

AACGTTCTTC GGGGCGTT (SEQ ID NO: 1)

Preferably, such partially single-stranded, dumbbell-shaped, covalently closed deoxyribonucleic acid molecule is constiuted by the ISS30 sequence, as follows:

(SEQ ID NO: 4)
CCTAGGGGTT ACCACCTTCA TTGGAAAACG TTCTTCGGGG

CGTTCTTAGG TGGTAACCCC TAGGGGTTAC CACCTTCATT

GGAAAACGTT CTTCGGGGCG TTCTTAGGTG GTAACC

Another aspect of the present invention relates to a partially single-stranded, dumbbell-shaped, covalently closed deoxyribonucleic acid molecule comprising at least one sequence selected from the group consisting of:
(a) the mini sequence as in SEQ ID NO: 2
GTTCCTGGAG ACGTTCTTAG GAACGTTCTC CTTGACGTTG GAGAGAAC,
(b) the AT-2L sequence as in SEQ ID NO: 3

ACCTTCCTTG TACTAACGTT GCCTCAAGGA AGGTTGATCT

TCATAACGTT GCCTAGATCA,
and (c) the base sequence as in SEQ ID NO: 1
AACGTTCTTC GGGGCGTT.

A further aspect of the present invention relates to a partially single-stranded, dumbbell-shaped, covalently closed deoxyribonucleic acid molecule comprising at least one sequence selected from the group consisting of:
(1) the mini sequence as in SEQ ID NO: 2
GTTCCTGGAG ACGTTCTTAG GAACGTTCTC CTTGACGTTG GAGAGAAC,
(2) the AT-2L sequence as in SEQ ID NO: 3

ACCTTCCTTG TACTAACGTT GCCTCAAGGA AGGTTGATCT

TCATAACGTT GCCTAGATCA,
(3) the ISS30 sequence as in SEQ ID NO: 4

CCTAGGGGTT ACCACCTTCA TTGGAAAACG TTCTTCGGGG

CGTTCTTAGG TGGTAACCCC TAGGGGTTAC CACCTTCATT

GGAAAACGTT CTTCGGGGCG TTCTTAGGTG GTAACC,
(4) the ISS30-ds sequence as in SEQ ID NO: 6

TCTTCGGGGC GTTCTTTACT AGGTCCTCTC CAGGTTACCA

CCTAAGAACG CCCCGAAGAA CGTTTTCCAA TGATACTAGG

TCCTCTCCAG GTTACCACCT TCATTGGAAA ACGT,
(5) the ISS30-sl sequence as in SEQ ID NO: 7

TCTTCGGGGC GTTCTTTTTT AAGAACGCCC CGAAGAACGT

TTTCCAATGA TTTTTCATTG GAAAACGT,
(6) the ISS13 sequence as in SEQ ID NO: 8

CCTAGGGGTT ACCACCTAAC GTTCTTCGGG AGGTGGTAAC

CCCTAGGGGT TACCACCTAA CGTTCTTCGG GAGGTGGTAA CC,
and (7) the AT-1L sequence as in SEQ ID NO: 9

```
CTTCCTTGTA CTAACCTTGC CTCAAGGAAG GTTGATCTTC
ATAACGTTGC CTAGATCAAC.
```

The partially single-stranded, dumbbell-shaped, covalently closed deoxyribonucleic acid molecule of the present invention can be used for immunostimulation in humans or other vertebrates.

The term "immunostimulation" is defined herein as activation of the effector cells of the immune system, in particular activation of the thymocytes such as T-helper cells, cytotoxic thymocytes, B cells, the so-called natural killer (NK) cells, macrophages, monocytes, dendritic cells and their predecessors, and other unknown cell populations that function within the immune system. These thymocytes are stimulated by the nucleic acid molecules of the present invention and therefore proliferate, migrate, differentiate, or otherwise become active. For example, a significant aspect of immunostimulation by the nucleic acid molecules of the present invention is the proliferation of B cells, without the costimulatory signal from helper thymocytes that is normally required for such B cells to proliferate.

The term "immunomodification" or "immunomodulation" is defined herein as influences upon the nature or character of an immunoreaction, besides the immunostimulation as defined hereinabove, either by affecting an immunoreaction that is currently developing or maturing, or by modulating the character of an immunoreaction that has been developed. An example of such immunomodification or immunomodulation is that under the influence of the nucleic acid molecules of the present invention, macrophages and monocytes typically release Interleukin-12, which then stimulates the secretion of interferon gamma by the NK cells and the helper thymocytes of the cytotoxic type. Interferon is a stimulator for a number of components (such as CD8-positive killer cells) in a cytotoxic, cell-mediated immunoresponse; it is also a potent antagonist for the production of soluble sub-type IgG1 antibody molecules mediated by Interleukin-4. The overall effect of the immunomodification or immunomodulation by the nucleic acid molecules of the present invention is the induction of a cytotoxic immunoresponse directed toward those pathogens to which a patient or test animal normally would react with an antibody-mediated immunoresponse, in absence of such nucleic acid molecules.

Other aspects and objects of the present invention are further presented and described by the following Figures, illustrations, examples, and claims.

DETAILED DESCRIPTION OF THE INVENTION

Figure 1:
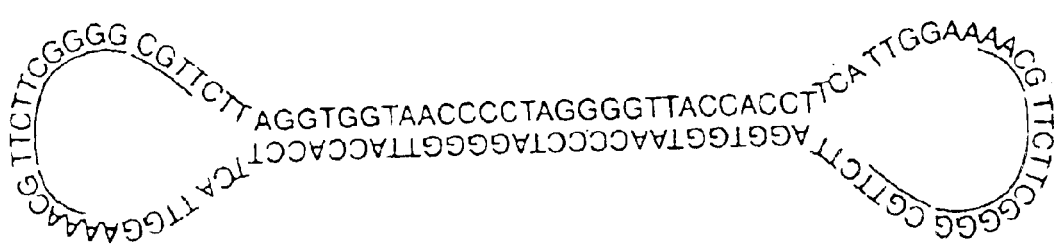
FIG. 1 shows the structure of a partially single-stranded, dumbbell-shaped, covalently closed nucleic acid molecule (ISS30 sequence as in SEQ ID NO: 4), according to one embodiment of the present invention.

In the past, efforts concerning production of stable ISS-ODN molecules have been concentrated mainly on introducing new, more tolerant base modification in single-strained linear constructs, because it is believed that only single-strained linear constructs are effective for immunostimulation or immunomodulation.

Surprisingly, the inventors of the present application have found that double-stranded molecules with the relevant ISS sequence in the double-stranded area also exhibit a significant stimulatory effect. It is also surprising to find that a partially single-stranded, covalently closed molecule having the stimulatory CpG motifs in its single-stranded stem loop area display not only a high level of stability in the serum, but also a high stimulatory effect comparable to that of an open-chain, single-stranded ISS molecule.

The partially single-stranded, dumbbell-shaped, covalently closed nucleic acid molecules of the present invention can therefore be used, in place of the conventional open-chain, single-stranded ISS molecules, for inducing strong stimulation of cellular immunoresponse, for modulating existing immunoresponse, or for otherwise influencing regulatory circuits. In comparison with the previously used open-chain, single-stranded ISS molecules, the covalently closed nucleic acid molecules of the present invention are much more stable and nontoxic in vivo.

Certain "weak" antigens, such as breakpoint peptides from chromosomal translocations or mutated oncogenes that often occur in tumor cells, are incapable of activating MHC-1 presentation that is required for triggering immunoresponses. Melief & Kast, *T-Cell Immunotherapy of Cancer*, Res. Immunol., 142 (5–6):425–9 (June–August 1991); Pasternak et al., *Chronic Myelogenous Leukemia: Molecular and Cellular Aspects*, J. Cancer Res. Clin. Oncol., 124(12):643–60 (1998). The covalently closed nucleic acid molecules containing immunostimulatory CpG motifs, as described hereinabove, can be used to induce an immunoresponse to those "weak" antigens. For example, they can be used as adjuvants in prophylactic vaccinations.

Such covalently closed nucleic acid molecules can also be used to break the tolerance to autoantigens such as the tyrosinase or tyrosinhydroxylase expressed in tumorous cells of the malignant melanoma and presented in MHC-1.

Moreover, it has been well-known that for a large number of pathogens, the specific type of immunoresponse induced thereby has a decisive influence on the course of the infection, or even on the patient's ability to survive such infection. Because most deleterious allergic reactions are caused by overreaction relating to a Type-2 immunoresponse, the covalently closed ISS molecules of the present invention can be used to repolarize the immunoreaction to an existing infection caused by a pathogen, i e., to change it from a Type-2 response to a Type-1 response, thus enabling the pathogen to be controlled or eliminated by Type-1 response instead of a Type-2 response that may cause allergic reaction.

It has also discovered that certain nucleic acid molecules containing CpGs function to neutralize ISS-induced stimulation (CpG-N), i.e. that molecules of this kind are able to suppress the stimulatory effect of the ISS sequences when added to them. Krieg et al., *Sequence Motifs in Adenoviral DNA Block Immune Activation by Stimulatory CpG Motifs*, Proc. Nat'l Acad. Sci. USA, 95(21):12631–6 (Oct. 13, 1998). There is at least one human disease, systemic lupus erythematosus, which is characterized by the confirmed existence of anti-DNA antibodies in patient serum, which may be caused by an immunoreaction to bacterial ISSs. In such case, blocking the immunoreactions stimulated by the bacterial ISSs using CpG-N motifs can provide a cure to the disease.

Another example of the clinical application of the ISS molecules of the present invention is in connection with the clinical manifestation of the allergy or an atopic reaction. Certain forms of this disease are characterized by the fact that, in the patients concerned, the plasma level for type E (IgE) immunoglobins is considerably higher than normal. This increased IgE level is not only a symptom of the disease, but also, using the signal transduction pathways of IgE bonding to effector cells in the immune system, and the subsequent release of chemokine and paracrine messenger substances, in particular histamine, it also constitutes significantly to the clinical manifestation of a local or systemic overreaction. Numerous research projects are engaged in trying to modulate this immunoresponse. Use of the ISS molecules of the present invention in treating patients therefore becomes one approach for immunomodulation.

Further beneficial aspects and features of the present invention are more fully apparent from the following examples:

EXAMPLE 1
Synthesis of ISS30 Nucleic Acid Molecules

5'-phosphorylated ODNs with the sequence CCTAGGGGTT ACCACCTTCA TTGGAAAACG TTCT-TCGGGG CGTTCTTAGG TGGTAACC (TIB-Molbiol, Berlin), as shown in SEQ ID NO: 5, were heated to a temperature of 90° C. for 5 minutes and subsequently cooled on ice to enable development of a stem-loop structure. Self-complementary overhangs of such ODNs were ligated with a final concentration of 1 μg/μl DNA in the presence of T4 DNA ligase (0.1 U/μg ODN) at 37° C. for 24 hours. The product was obtained following phenol extraction and subsequent extraction with chloroform as well as isopropanol precipitation in the present of $MgCl_2$ (final concentration— 10 mM) and NaAc (final concentration—300 mM), and after centrifugation and suspension in water.

In order to remove endotoxin contamination, the ligation product was subject to subsequent anion exchange chromatography (carrier substance: LiChrospher DMAE, Merck Darmstadt; 0–1M NaCl in 50 mM $Na_3PO_4$) and concentrated by isopropanol precipitation. For in vivo experiments, this method is carried out in sterile conditions and the end product is suspended in sterile PBS.

FIG. 1 shows the structure of the ISS30 sequence (SEQ ID NO:4), which is a partially single-stranded, dumbbell-shaped, covalently closed nucleic acid molecule that contains CpG motifs. The immunostimulatory portions of such molecule (i.e. the CpG motifs) are underlined. It is evident that such immunostimulatory portions exist in the two single-stranded stem-loops of such molecule.

EXAMPLE 2
Isolating Spleen Cells and Cell Culture and Cytokine Assays

Spleen cells were isolated from fresh spleens from 5 to 10-week old BALB/c mice (Bomholtgard Breeding & Research Center, Denmark). Two freshly isolated spleens were homogenized using a 40 μm metal filter, and the cells obtained were suspended in 20 ml RPMI 1640 (10% FCS, 100 U/ml penicillin and 100 μg/ml streptomycin, Biochrom, Berlin). Erythrocytes and platelets were removed by gradient centrifugation (Ficoll 1.077; Biochrom, Berlin). The cells were incubated in a final concentration of $10^6$ cells/ml at 37° C. in an incubator flushed with 5% $CO_2$.

$10^5$ freshly isolated spleen cells were incubated in 96-well plates for 24 hours with the structures produced according to Example 1. The concentration of the structures was equal to 2 μM. The cytokines in the supernatant fluid were measured using the ELISA method (Biosource, Blegium) in accordance with the description given by the ELISA manufacturer. At least three measurements were carried out for all measuring points.

Figure 2:
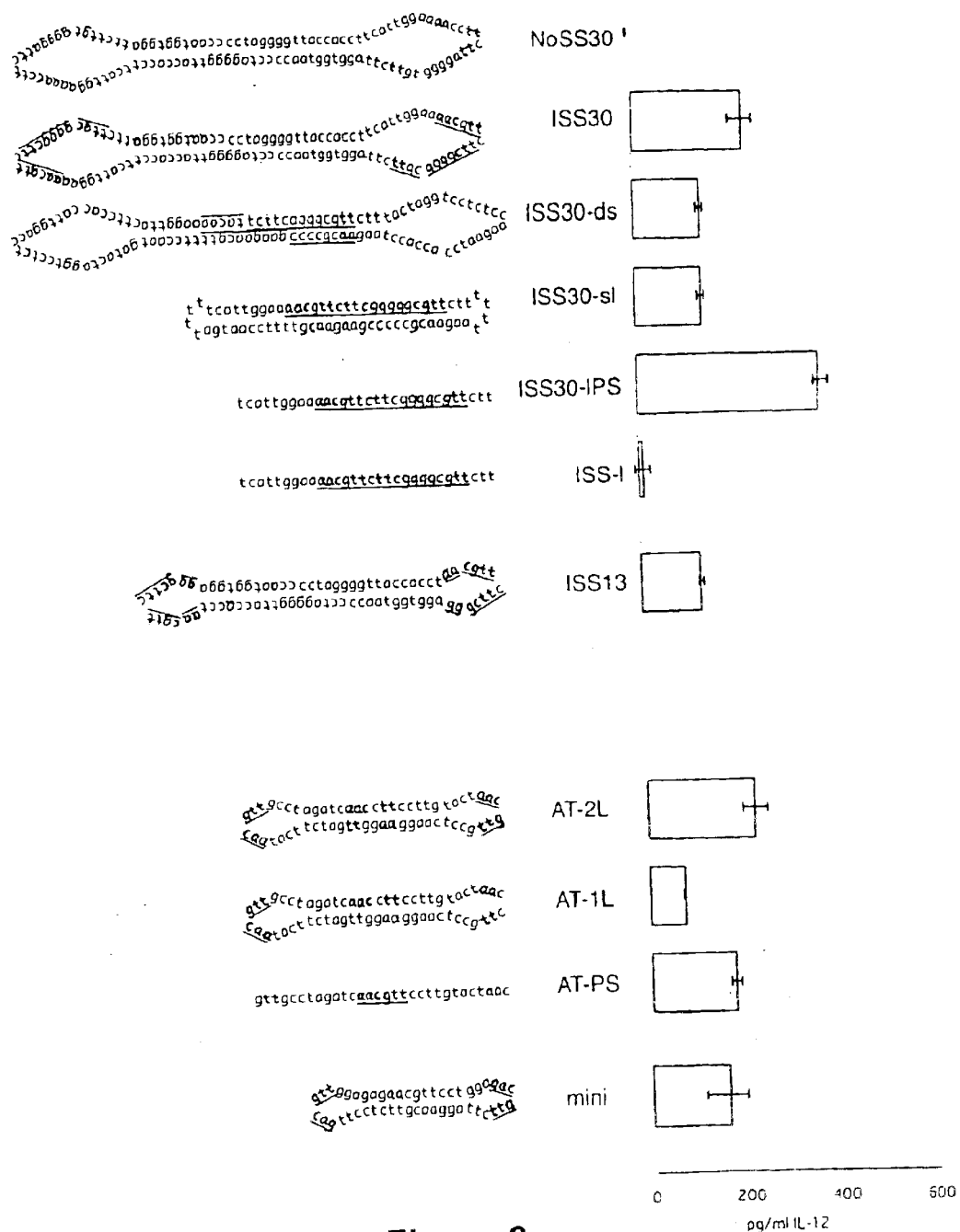
FIG. 2 shows the results of the IL-12 in vitro measurements in pg IL-12/ml, under the influences of various types of deoxyribonucleic acid molecules as shown on the left side, including NoSS30 (SEQ ID NO: 13), ISS30 (SEQ ID NO: 4), ISS30-ds (SEQ ID NO: 6), ISS30-sl (SEQ ID NO: 7), ISS30-IPS (SEQ ID NO: 10), ISS-I (SEQ ID NO: 11), ISS13 (SEQ ID NO: 8), AT-2L (SEQ ID NO: 3), AT-1L (SEQ ID NO: 9), AT-PS (SEQ ID NO: 12), and mini sequence (SEQ ID NO: 2).

The results of the experiment are shown in FIG. 2, comparing the IL-12 in vitro measurements for the following nucleic acid molecules:

| | |
|---|---|
| NoSS30 | SEQ ID NO: 13 |
| ISS30 | SEQ ID NO: 4 |
| ISS30-ds | SEQ ID NO: 6 |
| ISS30-sl | SEQ ID NO: 7 |
| ISS30-IPS | SEQ ID NO: 10 |
| ISS30-I | SEQ ID NO: 11 |
| ISS13 | SEQ ID NO: 8 |
| AT-2L | SEQ ID NO: 3 |
| AT-1L | SEQ ID NO: 9 |
| AT-PS | SEQ ID NO: 12 |
| Mini | SEQ ID NO: 2 |

Each ISS sequence (i.e. CpG motif) in the nucleic acid molecules is underlined.

The most active molecule is the phosphorothioate-protected, single-stranded linear molecule ISS30-IPS, which contains the base sequence AACGTTCTTC GGGGCGTT (SEQ ID NO: 1).

In contrast, the open-chain, single-stranded ISS30-I molecule that is unprotected hardly stimulates production of IL-12 at all, because such molecule is unstable and is degraded before production of IL-12 can be stimulated.

ISS30 molecule, which is a partially single-stranded, dumbbell-shaped, covalently closed nucleic acid molecule of the present invention, shows activity that is comparable with that of the ISS30-IPS molecule. ISS30 comprises two of the base sequence AACGTTCTTC GGGGCGTT (SEQ ID NO: 1), one at each single-stranded stem loop.

NoSS30 has the same structure and very similar sequence as those of the ISS30 molecule, except that it does not comprise the base sequence AACGTTCTTC GGGGCGTT (SEQ ID NO: 1). NoSS30 displays no activity at all.

Both ISS30-ds and ISS30-sl are partially single-stranded, dumbbell-shaped, covalently closed nucleic acid molecules that have ISS sequences in the double-stranded, linear area. In comparison to ISS30, these two molecules show significantly reduced effect, but they are still sufficiently effective.

ISS13, AT-2L, AT-1L and mini sequence are all short, partially single-stranded, dumbbell-shaped, covalently closed nucleic acid molecules that have ISS sequences in the single-stranded stem loop area, according to the present invention. They also exhibit significant effect. Note that the AT-1L with only one ISS sequence displays a reduced effect in comparison with AT-2L having two ISS sequences. Mini sequence shows that it is possible to reduce the molecule to a very short minimum length without sacrificing its effect.

EXAMPLE 3
Serum Stability

5 μg of the deoxyribonucleotide WTO-11-P (phosphate-GAAGAACGTT TTCCAATGAT TTTTCATTGG AAAAC)(SEQ ID NO: 14) (TIB Molbiol) were marked with 75 μCi gamma-32P-ATP (6000 Ci/mmol) (NEN) in the presence of 10μ T4 polynucleotide kinase (MBI-Fermentas, Leon-Rot) according to the manufacturer's specifications. The enzyme was inactivated by heating it to 75° C. over a period of 1 hour. The sediment was purified with water to 50 μl and by a ZG-50 size exclusion tube (Pharmacia). The radioactively marked molecule was converted with unmarked 5'-phosphorylated WOT-10-P (5'phosphate-GTTCTTCGGG GCGTTCTTTT TTAAGAACGC CCC) (SEQ ID NO: 15)(TIB Molbiol) in the presence of 1 U T4 DNA ligase (MBI-Fermentas, Leon-Rot) and 1 mM ATP at 37° C. for 2 hours. Unligated ODNs were removed by subsequent incubation with T7-DNA polymerase. The activity of the obtained preparation (ISS30-sl molecule as in SEQ ID NO: 7) was measured in a scintillation counter (Beckmann Instruments) at 78000 cpm/μl, equivalent to 7800 cpm/ng.

Figure 3:
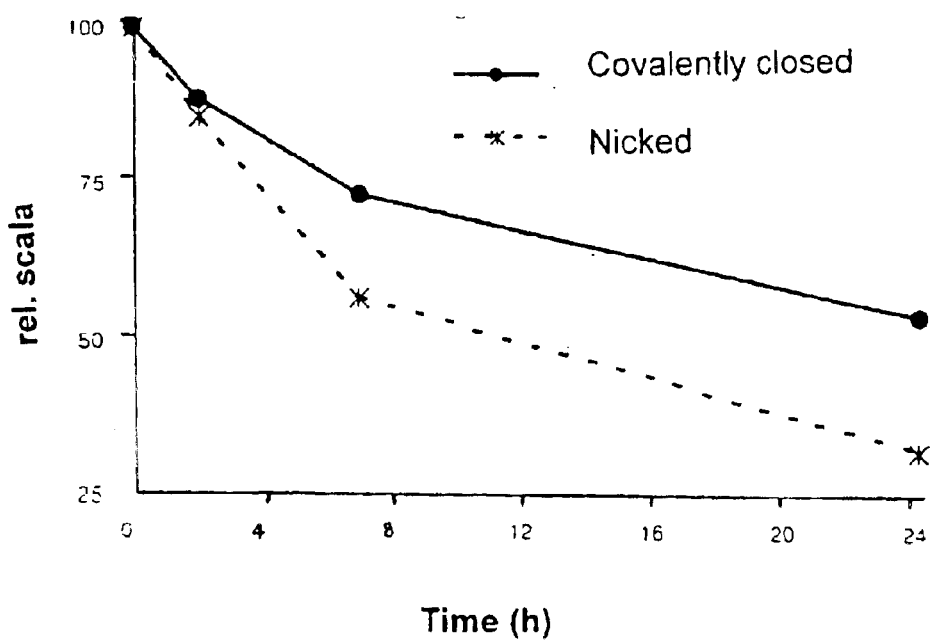
FIG. 3 shows the results of stability of the covalently closed ISS30-sl sequence in comparison with similar sequence with nicked ends.

In order to measure the stability of the structures obtained in the serum, 2.5 μl of the DNA (195.000 cpm equivalent to 25 ng DNA), together with 20 μl non-inactivated foetal calf serum (Life Technologies), alternatively, freshly obtained human serum from a test person, were added to 180 μl RPMI Medium (Life Technologies). All measurements were carried out three times. The samples were incubated at 37° C.; 20 μl aliquot samples were taken at 0, 1, 2, 7, 11, and 24 hours and stored at −40° C. Each 5 μl of the samples was digested by 20 μg/ml proteinase K (Life) over a period of 1 hour. The samples were subsequently subjected to denaturing polyacrylamide electrophoresis, the gels were digitalized (Molecular Dynamics) and the band intensity compared (IP labgel). The results of the evaluation are shown in FIG. 3. Every data item is the mathematical average of three measurements.

EXAMPLE 4
Administering the Structures in a Mouse

The structures of the present invention were tested in vivo. Six-week old female BALB/C mice were each intraperitoneally injected with 50 μg of the corresponding structures in 250 μl sterile PBS. 50 μl of blood was taken after 2, 6, 24, and 72 hours respectively, mixed with heparin, centrifuged, and the serum was then stored at −70° C. The samples were tested together for IL-12 using the ELISA method (see above). All preparations were tested for endotoxins using the endotoxin assay system (limulus amebocyte lysate (LAL) test, BioWhittaker). All the samples exhibited endotoxin amounts below identified levels.

EXAMPLE 5
Incubation of Human Peripheral Blood Mononuclear Cells (PBMC) with Circular ISS-ODNS PBMCs are isolated by the usual methods from the blood samples of a test person with an increased IgE level, and incubated in a concentration of $10^6$ cells per ml in RPMI medium (10% foetal calf serum (FCS)). The following are added respectively to the samples:

A: nothing (as control sample);
B: 1 μg/ml anti CD-40 antibodies, and 5 ng/ml IL-4;
C: 1 μg/ml anti CD-40 antibodies, 5 ng/ml IL-4, and 2 μM ODN ISS30 as described in SEQ ID NO: 4;
D: 2 μM ODN ISS30.

The cells are then incubated at 37° C. for 10 days in an incubator under normal cell culture conditions. The cells are then centrifuged and the IgE amount is determined from the supernatant fluid using the ELISA method. This produces the following results:

|  | A | B | C | D |
| --- | --- | --- | --- | --- |
| Test Person 1 | 9.2 ng/ml | 10.3 ng/ml | 3.8 ng/ml | 4.3 ng/ml |
| Test Person 2 | 4.6 ng/ml | 6.7 ng/ml | 1.7 ng/ml | 3.0 ng/ml |
| Test Person 3 | 1.5 ng/ml | 3.2 ng/ml | 0.6 ng/ml | 0.1 ng/ml |

EXAMPLE 6
In vivo Experiment to Highlight the Effect of ISS-30 when Immunizing Against the Hepatitis B Surface Antigen (HbsAg)

The effect of the structures as described hereinabove, which stimulate the immunoresponse, were tested in vivo. 6-week old female BALB/C mice with gene expression structures (Midge) coding for the hepatitis B surface antigen (HbsAg) were immunized. Five mice per group respectively, three groups in total, plus two control samples, were immunized intradermally with 10 μg DNA dissolved in 50 μl sodium phosphate pH 7.2. In order to test and compare the stimulating effect of the ODN-ISS30 (as described in SEQ ID NO: 4) with thioate-protected ISS-ODNs, these were additionally administered in a 10 μg concentration together with the injection.

Figure 4:
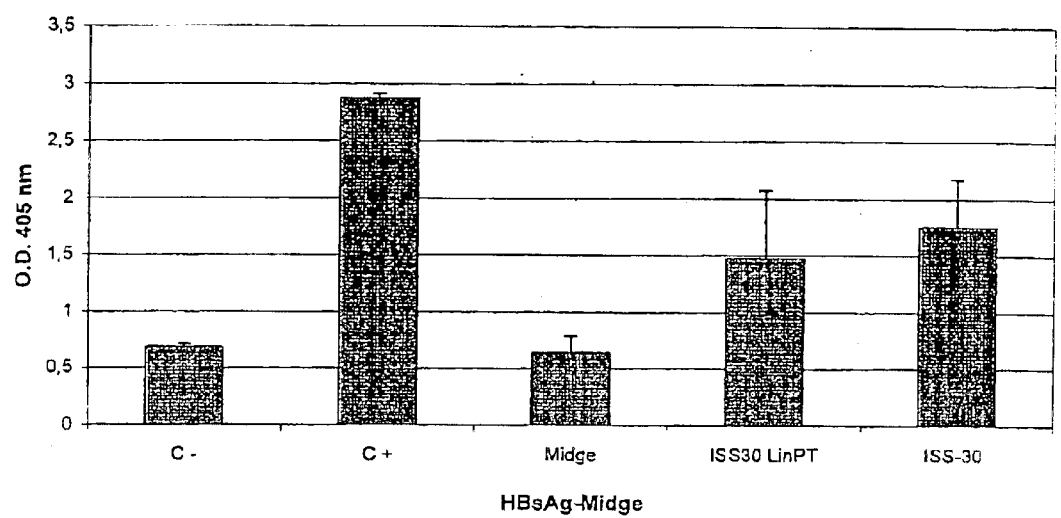
FIG. 4 shows the effect of ISS-ODNs when immunizing against a hepatitis B surface antigen (HbsAg).

FIG. 4 is an analysis of the overall IgG, HbsAg. The antibody titer was determined using the ELISA method, whereby the absorption in OD (optional density) was measured at a wavelength of λ=405 nm. Blood was taken after weeks 2, 3, 4, and 5. The values are from week 4.

The following applies:
C−: control: sera from mice that did not receive a DNA injection
C+: control: sera from mice that received a 70 μg DNA injection
Midge: Minimalistic Immunogenically Defined Gene Expression. Linear covalently closed expression cassettes consisting of the functions promoter, coding sequence and terminator of the corresponding gene sequence and a polyadenylic sequence.
ISS30 LinPT: linear immunostimulatory nucleic acid sequence of 30 bp, whose ends are protected by phosphorothioate against degradation by nucleases.
ISS30: dumbbell-shaped structures as described in the present invention.
The error marker bars highlight standard deviation.

Compared with the Midge group (no additional ISS-ODN administered), the adjuvancy effect of ODN-ISS30 is evident by the greatly increased level of antibody titers. In addition to the amplifying effect, the structures (as described in the invention) show a much improved effect compared with the thioate-protected structures.

Another aspect of the immunostimulation is the improved maturing of dendritic cells under the influence of ISS-ODN. An example of this is shown when isolating CD14, CD8, and CD4 positive cells.

(a) Isolating CD14, CD8, and CD4 positive cells.
CD 14 positive dendritic cells (DC) were isolated using magnetic particles (Milteniy Biotec, Bergisch Gladback, Germany) as per the manufacturer's instructions. To achieve this, mononuclear cells from the peripheral blood of healthy donors were isolated using a Ficoll density gradient (Pharmacia) and separated with the magnetic particles specific to the respective surface marker on the corresponding columns.

(b) Maturing of dendritic cells.
CD14 positive cells from a monocytic line were cultivated in CellGro medium (Cell Genix, Freiburg) which contained Glutamax 1 (Gibco Life, Karlsruhe), GM-CSF (800 U/ml, Leucomax 300; Novartis Parma GmbH) and IL-4 (500 U/ml, R&D Systems GmbH). On days three and five, respectively, half of the medium was replaced by the same quantity of fresh medium. On day seven, the entire medium was replaced and enriched with Prostaglandin E2 (1 µg/ml, Sigma), TNFa (20 ng/ml, Sigma), IL-6 (1000 U/ml, R&D Systems GmbH), and 2 µM of ISS30 as described hereinabove.

(c) IFN-gamma ELISpot assay.

Nitro-cellulose coated microtiter plates (96-fold) HA S45 (Milipore, Eschborn) were coated with anti-interferon (IFN) gamma (10 µg/ml, Mabtech) at 4° C. overnight and subsequently blocked with 5% human serum albumin (HSA) (Baxter, Unterschleißheim). The plates were washed and then incubated with (as described) 50 µl matured dendritic cells (DC) ($2\times10^5$/ml) and (as described) 50 µl isolated CD4-positive T-cells ($2\times10^6$/ml) at 37° C. for 72 hours and with 7% $CO_2$ with 100 µl of the corresponding antigens. 10 Lf Tetanus Toxoid (TT) (Chiron Behring GmbH & Co., Marburg) were used as antigens. After they had been thoroughly washed the plates were incubated with an IFN-gamma specific, biotinylated mouse antibody (5 µg/ml, Mabtech, Germany) the presence of which was verified with avidin-coupled alkaline phosphatase (Sigma-Aldrich, Steinheim) and a subsequent color reaction with BCIP/NBT (Sigma-Aldrich). The spots were evaluated with the help of computer-assisted video analysis (KS400 imaging system software, Carl Zeiss, Eching) on a Carl Zeiss Vision Axioplan 2 microscope.

The existence of ISS-ODNs as described in the invention caused a significant increase in the number of spots in the IFN-gamma ELISpot. In addition, during co-incubation of the dendritic cells and T-helper cells, the presence of ISS-ODNs considerably increased the antigen-specific nature of the reaction; thus the quotient of TT-specific (TT present during co-incubation on the ELISpot plate) to unspecific (no TT) spots changed from 8.9 (with ISS) to 2.8 (without ISS).

One feature (or aspect) of an embodiment of the invention resides broadly in a deoxyribonucleic acid molecule, consisting of a partially single-stranded, dumbbell-shaped, covalently closed chain of deoxyribonucleoside residues, and containing one or more sequences of the base sequence $N^1N^2CGN^3N^4$, whereby $N^1N^2$ is an element of the GT, GG, GA, AT or AA group, $N^3N^4$ is an element of the CT or TT group, as well as C deoxycytosine, G deoxyguanosine, A deoxyadenosine and T deoxythymidine, characterized by its sequence being a) GTTCCTGGAG ACGTTCTTAG GAACGTTCTC CTTGACGTTG GAGAGAAC or b) ACCTTCCTTG TACTAACGTT GCCTCAAGGA AGGTTGATCT TCATAACGTT GCCTAGATCA, or c) containing a deoxyribonucleic acid sequence of the base sequence AACG TTCTTCGGGG CGTT, and d) whereby the deoxyribonucleic acid molecule has a length of 40 to 200 nucleotides.

Another feature (or aspect) of an embodiment of the invention resides broadly in deoxyribonucleic acid molecules, whereby the base sequence from characteristic c) is contained in the sequence CCTAGGGGTT ACCACCTTCA TTGGAAAACG TTCTTCGGGG CGTTCTTAGG TGGTAACC CCTAGGGGTT ACCACCTTCA TTGGAAAACG TTCTTCGGGG CGTTCTTAGG TGGTAACC.

Yet another feature (or aspect) of an embodiment of the invention resides broadly in deoxyribonucleic acid molecules, whereby the deoxyribonucleic acid molecule has a preferred length of between 48 and 116 nucleotides.

Still another feature (or aspect) of an embodiment of the invention resides broadly in use of deoxyribonucleic acid molecules for immunostimulation applications in humans or higher animals.

A further feature (or aspect) of an embodiment of the invention resides broadly in use of deoxyribonucleic acid molecules, whereby the sequence of the base sequence $N^1N^2CGN^3N^4$ is in the single-stranded area.

Another feature (or aspect) of an embodiment of the invention resides broadly in use of deoxyribonucleic acid molecules, whereby stimulation can take place in vitro or in vivo.

Yet another feature (or aspect) of an embodiment of the invention resides broadly in use of deoxyribonucleic acid molecules as vaccine adjuvancy in therapeutic or prophylactic applications.

The components disclosed in the various publications, disclosed or incorporated by reference herein, may be used in the embodiments of the present invention, as well as equivalents thereof.

The appended drawings in their entirety, including all dimensions, proportions and/or shapes in at least one embodiment of the invention, are accurate and are hereby included by reference into this specification.

All, or substantially all, of the components and methods of the various embodiments may be used with at least one embodiment or all of the embodiments, if more than one embodiment is described herein.

All of the patents, patent applications and publications recited herein, and in the Declaration attached hereto, are hereby incorporated by reference as if set forth in their entirety herein.

All of the patents, patent applications or patent publications, which were cited in the International Search Report dated Aug. 10, 2000, and/or cited elsewhere are hereby incorporated by reference as if set forth in their entirety herein as follows: WO 98/18810 to Kline, et al.; EP 0 855 184 to Heeg, et al.; FR 2 732 971 to Genset; and WO 98/21322 to Junghans, et al.

The corresponding foreign and international patent publication applications, namely, Federal Republic of Germany Patent Application No. 199 35 756, filed Jul. 27, 1999, and DE-OS 199 35 756 and DE-PS 199 35 756, and International Application No. PCT/DE00/00565 filed Feb. 24, 2000, as well as their published equivalents, and other equivalents or corresponding applications, if any, in corresponding cases in the Federal Republic of Germany and elsewhere, and the references and documents cited in any of the documents cited herein, such as the patents, patent applications and publications, are hereby incorporated by reference as if set forth in their entirety herein.

All of the references and documents, cited in any of the documents cited herein, are hereby incorporated by reference as if set forth in their entirety herein. All of the documents cited herein, referred to in the immediately preceding sentence, include all of the patents, patent applications and publications cited anywhere in the present application.

The details in the patents, patent applications and publications may be considered to be incorporable, at applicant's option, into the claims during prosecution as further limitations in the claims to patentably distinguish any amended claims from any applied prior art.

Some examples of immunostimulants and methods of immunostimulation may possibly be found in the following U.S. Pat. No. 6,290,971, "Adjuvant compositions comprising a mineral salt and another immunostimulating compound;" U.S. Pat. No. 6,258,358, "Targeted immunostimulation with bispecific reagents;" U.S. Pat. No. 6,248,332, "Targeted immunostimulation with bispecific reagents;" U.S. Pat. No. 6,239,116, "Immunostimulatory nucleic acid molecules;" U.S. Pat. No. 6,228,371, "Mycobacterium tuberculosis DNA sequences encoding immunostimulatory peptides;" U.S. Pat. No. 6,225,292, "Inhibitors of DNA immunostimulatory sequence activity;" U.S. Pat. No. 6,221,882, "Methods for inhibiting immunostimulatory DNA associated responses;" U.S. Pat. No. 6,210,672, "Topical immunostimulation to induce Langerhans cell migration;" U.S. Pat. No. 6,210,662, "Immunostimulatory composition;" U.S. Pat. No. 6,207,646, "Immunostimulatory nucleic acid molecules;" U.S. Pat. No. 6,168,796, "Immunostimulating activity of *Streptococcus pneumoniae* serotype 8 oligosaccharides;" U.S. Pat. No. 6,099,855, "Therapeutic, production and immunostimulatory uses of biocidal compositions;" U.S. Pat. No. 6,096,307, "Compositions for immunostimulation containing *Echinacea angustofolia, bromelain,* and *lysozyme;*" U.S. Pat. No. 6,080,725, "Immunostimulating and vaccine compositions employing saponin analog adjuvants and uses thereof;" U.S. Pat. No. 6,080,409, "Immunostimulatory method;" U.S. Pat. No. 6,045,802, "Enhanced immune response to an antigen by a composition of a recombinant virus expressing the antigen with a recombinant virus expressing an immunostimulatory molecule;" U.S. Pat. No. 6,019,985, "Immunostimulation methods for providing disease protection in poultry;" U.S. Pat. No. 6,004,587, "Therapeutic, production and immunostimulatory uses of biocidal compositions;" U.S. Pat. No. 5,998,376, "Substance P treatment for immunostimulation;" U.S. Pat. No. 5,977,081, "Triterpene saponin analogs having adjuvant and immunostimulatory activity;" U.S. Pat. No. 5,976,546, "Immunostimulatory compositions;" U.S. Pat. No. 5,968,909, "Method of modulating gene expression with reduced immunostimulatory response;" U.S. Pat. No. 5,945,508, "Substance P treatment for immunostimulation;" U.S. Pat. No. 5,916,571, "Immunostimulating activity of *streptococcus* pneumoniae serotype 8 oligosaccharides;" U.S. Pat. No. 5,879,685, "Immunostimulating and immunopotentiating reconstituted influenza virosomes and vaccines containing them;" U.S. Pat. No. 5,861,430, "Benzopyran phenol derivates for use as antibacterial, antiviral or immunostimulating agents;" U.S. Pat. No. 5,855,901, "Immunostimulating activity of *Streptococcus pneumoniae* serotype 8 oligosaccharides;" U.S. Pat. No. 5,830,877, "Method, compositions and devices for administration of naked polynucleotides which encode antigens and immunostimulatory;" U.S. Pat. No. 5,830,511, "Therapeutic, production and immunostimulatory uses of biocidal compositions;" U.S. Pat. No. 5,786,334, "Hexapeptide having immunostimulatory activity;" U.S. Pat. No. 5,759,554, "Immunostimulatory bacterial cell wall traction;" 5,695,768, "Immunostimulating activity of *Streptococcus pneumoniae* serotype 8 oligosaccharides;" U.S. Pat. No. 5,665,383, "Methods for the preparation of immunostimulating agents for in vivo delivery;" U.S. Pat. No. 5,658,957, "Immunostimulating wound healing compositions and method for preparing and using same;" U.S. Pat. No. 5,639,852, "Immunostimulatory agents;" U.S. Pat. No. 5,633,261, "Immunostimulating swainsonine analogs;" U.S. Pat. No. 5,621,106, "Method of making immunostimulating swainsonine analogs;" U.S. Pat. No. 5,604,254, "Indole derivative having prolonged immunostimulating activity and pharmaceutical compositions therefrom;" U.S. Pat. No. 5,576,351, "Use of arginine as an immunostimulator;" U.S. Pat. No. 5,527,915, "Immunostimulating 6-aryl-5,6-dihydroimidazo[2,1-beta]thiazole derivatives;" U.S. Pat. No. 5,506,235, "Quinoline derivatives as immunostimulants;" 5,503,830, "Compounds having immunostimulating activity and methods of use thereof;" U.S. Pat. No. 5,466,809, "Process for the preparation of immunostimulating swainsonine analogs;" U.S. Pat. No. 5,466,669, "Immunostimulatory agent;" U.S. Pat. No. 5,441,942, "2'3'-dideoxy-2',3'-didehydro-7,8-disubstituted guanosines and their immunostimulative effect;" 5,336,666, "Immunostimulant drug based on polar glyopeptidolipids of mycobacterium chelonae;" U.S. Pat. No. 5,272,151, "Aminoacyl and oligopeptidyl derivatives of allopurinol exhibiting immunostimulatory activity, and pharmaceutical formulations containing these substances;" U.S. Pat. No. 5,250,296, "Immunostimulant agent containing interleukin-2 and 5'-deoxy-5-fluorouridine;" U.S. Pat. No. 5,225,400, "Immunostimulating peptides, a process for their preparation and pharmaceutical compositions containing them;" U.S. Pat. No. 5,219,578, "Composition and method for immunostimulation in mammals;" U.S. Pat. No. 5,212,192, "Immunostimulating 6-aryl-5,6-dihydroimidazo [2,1-b]thiazole derivatives;" U.S. Pat. No. 5,185,321, "Process for producing immunostimulants;" U.S. Pat. No. 5,183,667, "Therapeutic immunostimulation by Glombrella cingulata;" U.S. Pat. No. 5,166,141, "Immunostimulating 7-deaza-7-oxa- and 7-deaza-7-oxo-analogs of 8-substituted-guanine-9-(1'-beta-D-aldoglycosidyl) derivatives and methods of treating test animals;" U.S. Pat. No. 5,136,030, "Immunostimulating guanine derivatives, compositions and methods;" U.S. Pat. No. 5,093,318, "Immunostimulating guanosine derivatives and their pharmaceutical compositions;" U.S. Pat. No. 5,079,231, "Immunostimulating peptides, a process for their preparation and pharmaceutical compositions containing them;" U.S. Pat. No. 5,073,630, "Polymeric anhydride of magnesium and proteic ammonium phospholinoleate with antiviral, antineoplastic and immunostimulant properties;" U.S. Pat. No. 5,041,535, "Antileukemic and immunostimulant peptides;" U.S. Pat. No. 5,011,828, "Immunostimulating guanine derivatives, compositions and methods;" U.S. Pat. No. 5,008,116, "Immunostimulatory microsphere;" U.S. Pat. No. 4,938,956, "Synergistic immunostimulating composition and method;" U.S. Pat. No. 4,937,327, "Derivative of D.25, process for its preparation, its use as an immunostimulant, and pharmaceutical compositions containing the derivative;" U.S. Pat. No. 4,929,601, "Tripeptides useful as immunostimulants as well as in the prevention of metastases;" U.S. Pat. No. 4,910,296, "Medicaments containing alpha 1 thymosin fragments and having an immunostimulant action, and fragments of alpha 1 thymosin;" U.S. Pat. No. 4,880,803, "Method of inducing immunostimulating activity;" U.S. Pat. No. 4,874,844, "Tripeptide with immunostimulating activity;" U.S. Pat. No. 4,857,512, "Immunostimulating polysaccharides, method for using such, and pharmaceutical preparations containing them;" U.S. Pat. No. 4,851,388, "Heptanoyl-glu-asp-ala-amino acid immunostimulants;" U.S. Pat. No. 4,842,862, "Immunostimulating agents;" U.S. Pat. No. 4,801,578, "Muramylpeptide-glycoprotein immunostimulant derivatives, their preparation and their use in medication;" U.S. Pat. No. 4,767,743, "Peptide immunostimulants;" U.S. Pat. No. 4,755,382, "Immunostimulating method;" U.S. Pat. No. 4,744,985, "Novel substances having carcinostatic and immunostimulating activity, process for preparing the same and carcinostatic agent containing the same;" U.S. Pat. No. 4,737,521, "Suramin sodium for use as an immunostimulant;" U.S. Pat. No. 4,734,403, "Membrane polysaccharides which are useful as immunostimulants;" U.S. Pat. No. 4,720,500, "N-1,8-naphthyridin-2-yl amides useful as immunostimulants;" U.S. Pat. No. 4,659,603, "Immunostimulating agents;" U.S. Pat. No. 4,650,788, "Novel peptides having an immunostimulating action, processes for their preparation and their use;" U.S. Pat. No. 4,619,915, "Peptide-substituted heterocyclic immunostimulants;" U.S. Pat. No. 4,596,709, "Novel immunostimulating glycoproteins;" 4,591,558, "Novel substances having antitumor and immunostimulating activity, process for preparing the same and antitumor agent containing the same;" U.S. Pat. No. 4,578,399, "Use of the diterpene derivative forskolin for immunostimulation;" U.S. Pat. No. 4,565,653, "Acyltripeptide immunostimulants;" U.S. Pat. No. 4,547,462, "Process for preparing substance having carcinostatic and immunostimulating activity;" U.S. Pat. No. 4,528,188, "Polysaccharide PS-A obtained from barrenwort deriving from plants belonging to the genus *Epimedium*, process for preparation thereof and phylactic and immunostimulating agents comprising said polysaccharide PS-A effective component;" 4,510,129, "Immunostimulating agent;" 4,501,693, "Method of preparing immunostimulant proteoglycans which induce production of interferon, proteoglycans obtained and pharmaceutical compositions containing them;" U.S. Pat. No. 4,478,828, "Nonapeptide having immunostimulative activity, process for the preparation thereof, and its use;" U.S. Pat. No. 4,477,437, "Substances having carcinostatic and immunostimulating activity;" U.S. Pat. No. 4,470,926, "Medicaments containing thymosin alpha 1 fragments and having an immunostimulant action, and fragments of thymosin alpha 1;" U.S. Pat. No. 4,412,946, "Immunostimulating glycoproteins;" U.S. Pat. No. 4,407,825, "Novel bis- and poly-disulfides having immunostimulant activity;" U.S. Pat. No. 4,399,124, "Peptides having immunostimulating properties and pharmaceutical compositions containing them;" U.S. Pat. No. 4,397,848, "N-Substituted aziridine-2-carboxylic acid immunostimulant derivatives;" U.S. Pat. No. 4,389,396, "Immunostimulating preparations based on ribosomal RNA's and a process for the preparation of the RNA's;" U.S. Pat. No. 4,376,731, "1-Aziridine carboxylic acid derivatives with immunostimulant activity;" U.S. Pat. No. 4,372,949, "Treatment of cancer with carcinostatic and immunostimulating agent containing lysophospholipid and phospholipid;" U.S. Pat. No. 4,337,243, "Immunostimulant medicament and process of preparing same;" and U.S. Pat. No. 4,285,930, "Antigens comprising immunostimulant adjuvants and their use in immunotherapy."

Some examples of immunostimulants, immunostimulation methods, immune system treatments, and vaccinations, using nucleic acids with CpG motifs, may possibly be found in the following U.S. Pat. No. 6,239,116, "Immunostimulatory nucleic acid molecules;" U.S. Pat. No. 6,225,292, "Inhibitors of DNA immunostimulatory sequence activity;" U.S. Pat. No. 6,221,882, "Methods for inhibiting immunostimulatory DNA associated responses;" U.S. Pat. No. 6,207,646, "Immunostimulatory nucleic acid molecules;" U.S. Pat. No. 5,968,909, "Method of modulating gene expression with reduced immunostimulatory response;" U.S. Pat. No. 6,339,068, "Vectors and methods for immunization or therapeutic protocols;" U.S. Pat. No. 6,239,116, "Immunostimulatory nucleic acid molecules;" U.S. Pat. No. 6,225,292, "Inhibitors of DNA immunostimulatory sequence activity;" U.S. Pat. No. 6,221,882, "Methods for inhibiting immunostimulatory DNA associated responses;" U.S. Pat. No. 6,218,371, "Methods and products for stimulating the immune system using immunotherapeutic oligonucleotides and cytokines;" U.S. Pat. No. 6,214,806, "Use of nucleic acids containing unmethylated CPC dinucleotide in the treatment of LPS-associated disorders;" U.S. Pat. No. 6,207,646, "Immunostimulatory nucleic acid molecules;" U.S. Pat. No. 6,194,388, "Immunomodulatory oligonucleotides;" U.S. Pat. No. 6,180,614, "DNA based vaccination of fish;" U.S. Pat. No. 6,090,791, "Method for inducing mucosal immunity;" U.S. Pat. No. 6,034,230, "Nucleic acids encoding myocardial peptides;" U.S. Pat. No. 5,962,636, "Peptides capable of modulating inflammatory heart disease;" and U.S. Pat. No. 5,780,448, "DNA-based vaccination of fish."

The invention as described hereinabove in the context of the preferred embodiments is not to be taken as limited to all of the provided details thereof, since modifications and variations thereof may be made without departing from the spirit and scope of the invention.

PARTIAL SUMMARY OF SEQUENCE DESCRIPTIONS

1. AT-1L (one CpG sepuence in the loop) Sequence of 60 bp
CTTCCTTGTACTAACCTTGCCTCAAGGAAGGTTGATCTTCATAACGTTGCCTAGATC
AAC 2. AT-2L (two CpG's in the loop) 60 bp
ACCTTCCTTGTACTAACGTTGCCTCAAGGAAGGTTGATCTTCATAACGTTGCCTAGA
TCA 3. AT-PS (Phosphorothioate on the ends) 30 bp
GTTGCCTAGATCAACGTTCCTTGTACTAAC 4. ISS-L (ISS in linear form), 30 bp
TCATTGGAAAACGTTCTTCGGGGCGTTCTT 5. ISS30-LPS (ILinear and protected with phosphorothioate), 30 bp
TCATTGGAAAACGTTCTTCGGGGCGTTCTT 6. NoSS30 (Contains no CpG's, control), 116 bp
CCTAGGGGTTACCACCTTCATTGGAAAACCTTCTTAGGGGTGTTCTTAGGTGGTAA
CCCCTAGGGGTTACCACCTTCATTGGAAAACCTTCTTAGGGGTGTTCTTAGGTGGT
AACC 7. ISS30, 116 bp -continued

PARTIAL SUMMARY OF SEQUENCE DESCRIPTIONS

CCTAGGGGTTACCACCTTCATTGGAAAACGTTCTTCGGGGCGTTCTTAGGTGGTAA
CCCCTAGGGGTTACCACCTTCATTGGAAAACGTTCTTCGGGGCGTTCTTAGGTGGT
AACC 8. mini, 48 bp
GTTCCTGGAGACGTTCTTAGGAACGTTCTCCTTGACGTTGGAGAGAAC 9. ISS13, 82 bp
CCTAGGGGTTACCACCTAACGTTCTTCGGGAGGTGGTAACC
CCTAGGGGTTACCACCTAACGTTCTTCGGGAGGTGGTAACC 10. ISS30-ds (CPG's are in the double strand), 114 bp
TCTTCGGGGCGTTCTTTACTAGGTCCTCTCCAGGTTACCACCTAAGAACGCCCCGA
AGAACGTTTTCCAATGATACTAGGTCCTCTCCAGGTTACCACCTTCATTGGAAAAC 11. ISS30-sL (CpG's in the double strand but with short loop), 68 bp
TCTTCGGGGCGTTCTTTTTTAAGAACGCCCCGAAGAACGTTTTCCAATGATTTTTCA
TTGGAAAACGT

Bibliography

The following listed publications are hereby expressly incorporated by reference as if set forth in their entirety herein.

1. Krieg et al., *CpG Motifs in Bacterial DNA Trigger Direct B-Cell Activation*, Nature 374:6522 546–9 (Apr. 6, 1995).
2. Sedar & Paul, *Acquisition of Lumphokine-Producing Phenotype by CD4+T Cells*, Annual Rev. Immunol., 12:635–73 (1994).
3. Melief & Kast, *T-Cell Immunotherapy of Cancer*, Res. Immunol., 142 (5–6):425–9 (June–August 1991).
4. Pasternak et al., *Chronic Myelogenous Leukemia: Molecular and Cellular Aspects*, J. Cancer Res. Clin. Oncol., 124(12):643–60 (1998).
5. Weber et al., *Tumor Immunity and Autoimmunity Induced by Immunization with Homologous DNA*, J. Clin. Invest., 102(6):1258–64 (Sep. 15, 1998).
6. Surman et al., *Generation of Polydonal Rabbit Antisera to Mouse Melanoma Associated Antigens Using Gene Gun Immunization*, Immunol. Methods, 214(1–2):51–62 (May 1, 1998).
7. Kovarik et al., *CpG Oligodeoxynucleotides can Circumvent the Th2 Polarization of Neonatal Responses to Vaccines but May Fail to Fully Redirect Th2 Responses Established by Neonatal Priming*, J. Immunol., 162(3) :1611–7 (Feb. 1, 1999).
8. Krieg et al., *Sequence Motifs in Adenoviral DNA Block Immune Activation by Stimulatory CpG Motifs*, Proc. Nat'l Acad. Sci. USA, 95(21):12631–6 (Oct. 13, 1998).
9. Krieg et al., *CpG DNA: A Pathogenic Factor in Systemic Lupus Erythematosus?*, J. Clin. Immunol., 15(6):284–92 (November 1995).
10. WO98/18810 A1.
11. Sheehan & Lan, Blood 92, 1617–25 (1998).
12. U.S. Pat. No. 5,663,153.
13. U.S. Pat. No. 5,723,335.
14. U.S. Pat. No. 5,858,462.
15. U.S. Pat. No. 5,750,669.
16. Hoson et al., Biochim. Biophys. Acta. 244, 339–344 (1995).
17. Lim et al., Nuc. Acids Res. 25, 575–581 (1997).
18. Blumenfeld et al., Nuc. Acids. Res. 21, 3405–3411 (1993).
19. Weeratna et al., *Reduction of Antigen Expression from DNA Vaccines by Coadministered Oligodeoxynucleotides*, Antisense Nucleic Acid Drug Dev., 8(4):351–6 (August 1998).
20. Walker et al., *Immunostimulatory Oligodeoxynucleotides Promote Protective Immunity and Provide Systemic Therapy for Leishmaniasis via IL-12-and IFN-Gamma-Dependent Mechanisms*, Proc. Nat'l Acad. Sci. USA, 96(12):6970–5 (Jun. 8, 1999).

What is claimed is:

1. A deoxyribonucleic acid molecule, consisting of a partially single-stranded, dumbbell-shaped, covalently closed chain of deoxyribonucleoside residues, and containing one or more sequences of the base sequence $N^1N^2CGN^3N^4$, wherein $N^1N^2$ is an element of the GT, GG, GA, AT or AA group, $N^3N^4$ is an element of the CT or TT group, as well as C deoxycytosine, G deoxyguanosine, A deoxyadenosine and T deoxythymidine, wherein its sequence contains a deoxyribonucleic acid sequence of the base sequence AACG TTCTTCGGGG CGTT (SEQ. ID No. 1), and wherein the deoxyribonucleic acid molecule has a length of 40 to 200 nucleotides.

2. The deoxyribonucleic acid molecule in accordance with claim 1, wherein the base sequence (SEQ. ID No. 1) is contained in the sequence (SEQ. ID No. 4)
CCTAGGGGTT ACCACCTTCA TTGGAAAACG TTCTTCGGGG

CGTTCTTAGG TGGTAACC CCTAGGGGTT ACCACCTTCA

TTGGAAAACG TTCTTCGGGG CGTTCTTAGG TGGTAACC.

3. The deoxyribonucleic acid molecule in accordance with claim 1, wherein the sequence of the base sequence $N^1N^2CGN^3N^4$ is in the single-stranded area.

4. A deoxyribonucleic acid molecule, consisting of a partially single-stranded, dumbbell-shaped, covalently closed chain of deoxyribonucleoside residues, and containing one or more sequences of the base sequence $N^1N^2CGN^3N^4$, wherein $N^1N^2$ is an element of the GT, GG, GA, AT or AA group, $N^3N^4$ is an element of the CT or TT group, as well as C deoxycytosine, G deoxyguanosine, A deoxyadenosine or T deoxythymidine, wherein its sequence contains a deoxyribonucleic acid sequence of the base sequence AACG TTCTTCGGGG CGTT (SEQ. ID No. 1).

5. The deoxyribonucleic acid molecule in accordance with claim 4, wherein the base sequence (SEQ. ID No. 1) is contained in the sequence (SEQ. ID No. 4)
CCTAGGGGTT ACCACCTTCA TTGGAAAACG TTCTTCGGGG

CGTTCTTAGG TGGTAACC CCTAGGGGTT ACCACCTTCA

TTGGAAAACG TTCTTCGGGG CGTTCTTAGG TGGTAACC.

6. The deoxyribonucleic acid molecule in accordance with claim 5, wherein the sequence of the base sequence $N^1N^2CGN^3N^4$ is in the single-stranded area.

7. The deoxyribonucleic acid molecule in accordance with claim 4, wherein the deoxyribonucleic acid molecule has a length of between 48 and 116 nucleotides.

8. The deoxyribonucleic acid molecule in accordance with claim 4, wherein the sequence of the base sequence $N^1N^2CGN^3N^4$ is in the single-stranded area.

* * * * *

UNITED STATES PATENT AND TRADEMARK OFFICE
CERTIFICATE OF CORRECTION

PATENT NO. : 6,849,725 B2
DATED : February 1, 2005
INVENTOR(S) : Claas Junghans et al.

It is certified that error appears in the above-identified patent and that said Letters Patent is hereby corrected as shown below:

Title page,
Item [56], References Cited, OTHER PUBLICATIONS,
"Kreig AM" reference, delete ":204" and insert -- :284 --.
"Sheehan and Lan" reference, delete "Tanase" and insert -- Tenase --.
"Clusel C et al." reference, delete "Hanomolar" and insert -- Nanonolar --.
"Weeratna R" reference, delete "Dumbell" and insert -- Dumbbell --.
"Erie D et al." reference, delete "Dumbell" and insert -- Dumbbell --.

Signed and Sealed this

Seventh Day of March, 2006

JON W. DUDAS
*Director of the United States Patent and Trademark Office*

SEQUENCE LISTING

<160> NUMBER OF SEQ ID NOS: 15

<210> SEQ ID NO 1
<211> LENGTH: 18
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (1)..(18)
<223> OTHER INFORMATION: Base sequence

<400> SEQUENCE: 1
aacgttcttc ggggcgtt                                                    18

<210> SEQ ID NO 2
<211> LENGTH: 48
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (1)..(48)
<223> OTHER INFORMATION: Mini sequence: circular single-stranded with
      stem loop structure (dumbbell), all phosphodiester

<400> SEQUENCE: 2
gttcctggag acgttcttag gaacgttctc cttgacgttg gagagaac                    48

<210> SEQ ID NO 3
<211> LENGTH: 60
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (1)..(60)
<223> OTHER INFORMATION: AT-2L sequence: circular single-stranded with
      stem loop structure(dumbbell), all phosphodiester

<400> SEQUENCE: 3
accttccttg tactaacgtt gcctcaagga aggttgatct tcataacgtt gcctagatca        60

<210> SEQ ID NO 4
<211> LENGTH: 116
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (1)..(116)
<223> OTHER INFORMATION: ISS30 sequence: circular single-stranded with
      stem loop structure (dumbbell), all phosphodiester

<400> SEQUENCE: 4
cctaggggtt accaccttca ttggaaaacg ttcttcgggg cgttcttagg tggtaacccc        60
taggggttac caccttcatt ggaaaacgtt cttcggggcg ttcttaggtg gtaacc          116

<210> SEQ ID NO 5
<211> LENGTH: 58
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (1)..(58)
<223> OTHER INFORMATION: 5'-phosphorylated oligodeoxyribonucleotide

<400> SEQUENCE: 5
cctaggggtt accaccttca ttggaaaacg ttcttcgggg cgttcttagg tggtaacc         58

<210> SEQ ID NO 6
<211> LENGTH: 114
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (1)..(114)
<223> OTHER INFORMATION: ISS30-ds sequence: circular single-stranded with
      stem loop structure (dumbbell), all phosphodiester

<400> SEQUENCE: 6
tcttcggggc gttctttact aggtcctctc caggttacca cctaagaacg ccccgaagaa    60
cgttttccaa tgatactagg tcctctccag gttaccacct tcattggaaa acgt    114

<210> SEQ ID NO 7
<211> LENGTH: 68
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (1)..(68)
<223> OTHER INFORMATION: ISS30-sl sequence: circular single-stranded with
      stem loop structure (dumbbell), all phosphodiester

<400> SEQUENCE: 7
tcttcggggc gttcttttt aagaacgccc cgaagaacgt tttccaatga tttttcattg    60
gaaaacgt    68

<210> SEQ ID NO 8
<211> LENGTH: 82
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (1)..(82)
<223> OTHER INFORMATION: ISS13 sequence: circular single-stranded with
      stem loop structure (dumbbell), all phosphodiester

<400> SEQUENCE: 8 cctagggggtt accacctaac gttcttcggg aggtggtaac ccctagggggt taccacctaa    60 cgttcttcgg gaggtggtaa cc    82

<210> SEQ ID NO 9
<211> LENGTH: 60
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (1)..(60)
<223> OTHER INFORMATION: AT-1L sequence: circular single-stranded with
      stem loop structure
      (dumbbell), all phosphodiester

<400> SEQUENCE: 9
cttccttgta ctaaccttgc ctcaaggaag gttgatcttc ataacgttgc ctagatcaac    60

<210> SEQ ID NO 10
<211> LENGTH: 30
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (1)..(30)
<223> OTHER INFORMATION: ISS30-IPS sequence: linear single-stranded
      sequence, first five and last three phosphoester linkages by
      thioate

<400> SEQUENCE: 10
tcattggaaa acgttcttcg gggcgttctt    30

<210> SEQ ID NO 11
<211> LENGTH: 30
<212> TYPE: DNA

```
<213> ORGANISM: Artificial Sequence
<220> FEATURE:
<223> OTHER INFORMATION: Synthetic Construct
<221> NAME/KEY: misc_feature
<222> LOCATION: (1)..(30)
<223> OTHER INFORMATION: ISS30-I sequence: linear single-stranded
      sequence, all phosphodiester

<400> SEQUENCE: 11
tcattggaaa acgttcttcg gggcgttctt                                      30

<210> SEQ ID NO 12
<211> LENGTH: 30
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (1)..(30)
<223> OTHER INFORMATION: AT-PS sequence: linear single-stranded sequence,
      first five and last three phosphoester linkages by thioate

<400> SEQUENCE: 12
gttgcctaga tcaacgttcc ttgtactaac                                      30

<210> SEQ ID NO 13
<211> LENGTH: 116
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (1)..(116)
<223> OTHER INFORMATION: NoSS30 sequence: circular single-stranded with
      stem loop structure (dumbbell), all phosphodiester

<400> SEQUENCE: 13
cctaggggtt accaccttca ttggaaaacc ttcttagggg tgttcttagg tggtaacccc     60 tagggttac caccttcatt ggaaaacctt ctagggtg ttcttaggtg gtaacc           116

<210> SEQ ID NO 14
<211> LENGTH: 35
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (1)..(35)
<223> OTHER INFORMATION: Deoxyribonucleotide WOT-11-P

<400> SEQUENCE: 14
gaagaacgtt ttccaatgat ttttcattgg aaaac                                35

<210> SEQ ID NO 15
<211> LENGTH: 33
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (1)..(33)
<223> OTHER INFORMATION: Deoxyribonucleotide WOT-10-P

<400> SEQUENCE: 15
gttcttcggg gcgttctttt ttaagaacgc ccc                                  33
```